United States Patent
Guo et al.

(10) Patent No.: US 6,491,660 B2
(45) Date of Patent: Dec. 10, 2002

(54) FRONTAL INFUSION SYSTEM FOR INTRAVENOUS BURRS

(75) Inventors: Zihong Guo, Bellevue, WA (US); Verivada Chandru Chandrasekaran, Mercer Island, WA (US); Tim J. Johnson, Seatac, WA (US); Brandon J. Shuman, Kirkland, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 42 days.

(21) Appl. No.: 09/768,745

(22) Filed: Jan. 23, 2001

(65) Prior Publication Data

US 2002/0099367 A1 Jul. 25, 2002

(51) Int. Cl.[7] .............................................. A61M 1/00
(52) U.S. Cl. ........................... 604/35; 604/19; 604/22; 604/43; 604/41; 606/159; 606/167
(58) Field of Search ............................. 604/19, 22, 35, 604/40, 41, 43; 606/159, 167, 168

(56) References Cited

U.S. PATENT DOCUMENTS

| | | | | |
|---|---|---|---|---|
| 4,715,538 A | * | 12/1987 | Lingnau ..................... 239/248 |
| 4,749,376 A | * | 6/1988 | Kensey et al. ................ 604/22 |
| 4,950,238 A | * | 8/1990 | Sullivan ....................... 604/22 |
| 4,990,134 A | | 2/1991 | Auth |
| 5,030,201 A | * | 7/1991 | Palestrant .................... 604/22 |
| 5,125,425 A | * | 6/1992 | Folts et al. .................. 134/167 |
| 5,154,724 A | * | 10/1992 | Andrews .................... 606/159 |
| 5,273,526 A | | 12/1993 | Dance et al. |
| 5,318,576 A | * | 6/1994 | Plassche, Jr. et al. ........ 606/159 |
| 5,356,418 A | * | 10/1994 | Shturman ................... 606/159 |
| 5,556,405 A | * | 9/1996 | Lary ............................ 606/159 |
| 5,667,490 A | * | 9/1997 | Keith et al. ................... 604/22 |
| 5,681,336 A | * | 10/1997 | Clement et al. ............ 606/159 |
| 5,792,157 A | * | 8/1998 | Mische et al. .............. 606/159 |
| 5,843,103 A | * | 12/1998 | Wulfman .................... 606/159 |
| 5,899,912 A | * | 5/1999 | Eaves, III ................... 606/159 |
| 5,901,906 A | * | 5/1999 | Bouldin ....................... 239/229 |
| 5,997,558 A | * | 12/1999 | Nash ......................... 606/159 |
| 6,015,420 A | * | 1/2000 | Wulfman et al. ........... 606/168 |
| 6,080,170 A | * | 6/2000 | Nash et al. ................. 606/159 |
| 6,096,054 A | * | 8/2000 | Wyzgala et al. ............ 606/170 |
| 6,126,667 A | * | 10/2000 | Barry et al. ................ 606/159 |
| 6,146,395 A | * | 11/2000 | Kanz et al. ................. 606/159 |
| 6,156,048 A | * | 12/2000 | Wulfman et al. ........... 606/159 |
| 6,221,087 B1 | * | 4/2001 | Anderson et al. .......... 606/159 |
| 6,319,242 B1 | * | 11/2001 | Patterson et al. ........... 604/508 |
| 6,328,750 B1 | * | 12/2001 | Berry et al. ................. 606/168 |

FOREIGN PATENT DOCUMENTS

DE      197 34 890 C1     7/1999

OTHER PUBLICATIONS

Int'l Search Report (EPO) dated May 29, 2002, Application No. PCT/US01/43243, filed Nov. 20, 2001 (Applicant: SciMed Life Systems, Inc.).

* cited by examiner

*Primary Examiner*—Henry C. Yuen
*Assistant Examiner*—Frederick C. Nicolas
(74) *Attorney, Agent, or Firm*—Christensen O'Connor Johnson Kindness PLLC (57) ABSTRACT

Infusion liquid is expelled distally of an ablation burr for washing a blood vessel lesion being treated by the burr. The infusion liquid can be aspirated in a proximate direction to carry the infusion liquid and loose ablated particles of the lesion away from the treatment area. The infusion liquid can be supplied through one or more passages in the burr, In addition to distally extending passages, the burr can include transverse passages extending at least partly in a proximate direction, with the distally extending and proximately extending passages sized so that only a minor portion of the infusion liquid is expelled distally.

15 Claims, 5 Drawing Sheets

FRONTAL INFUSION SYSTEM FOR INTRAVENOUS BURRS

FIELD OF THE INVENTION

The present invention relates to medical devices in general, and in particular to ablation systems for revascularizing occluded blood vessels.

BACKGROUND OF THE INVENTION

A common technique for treating partially or totally occluded cardiac vessels is cardiac bypass surgery. With this procedure, a surgeon harvests a vessel from another part of the patient's body. The harvested vessel is grafted to healthy sites in the cardiac vessels in order to direct blood flow around a blockage or around unhealthy tissue of the heart muscle. For example, a portion of the saphenous vein may be used, resulting in what is referred to as a saphenous vein graft or SVG.

However, SVG's also may become occluded within a few years of being grafted onto the heart muscle. The material that occludes SVG's can be more loosely organized and brittle than the material that occludes native cardiac vessels. As a consequence, treating occluded SVG's can be more difficult because the occluding material tends to break off and can flow downstream where it becomes trapped or causes a blockage.

One method of treating vein graft lesions is described in U.S. Pat. No. 5,681,336. That patent discloses a system of ablating vein graft lesions by use of proximal and distal balloons that isolate the treatment area. Ablated material is aspirated. Infusion of liquid may be used to maintain vascular pressure and prevent the grafted vein from collapsing during aspiration. Specially designed burrs are used to abrade a lesion in the vein, and the abraded material is aspirated through a catheter that extends into the treatment area. Nevertheless, there is some concern that not all of the ablated material will be aspirated so that, following treatment, such material may be carried downstream.

SUMMARY OF THE INVENTION

The present invention provides an improved system for ablation of blood vessel lesions using both aspiration for removal of ablated material and infusion directed distally (frontally) for washing the treated area. The amount of frontal infusion for washing purposes is carefully controlled so that the ablated material still flows proximally (rearward) into an aspiration catheter. The proximal end portion of the area to be treated can be isolated by use of a balloon or other blocking device. The distal portion of the treatment area also may be blocked, to assist in directing the forward flow of the infusion liquid, or the flow rate of infusion liquid can be carefully controlled so as not to direct ablated material distally away from the treated area. For example, the respective degrees of aspiration and frontal infusion can be controlled to assure that all distally directed infusion liquid is aspirated proximally, carrying with it any loose material.

The infusion liquid can be conveyed through an axial bore of a flex shaft to an ablation burr movable along a guide wire. The burr can be provided with passages for expelling the infusion liquid, including passages directed distally along the guide wire and/or passages through the distal portion of the burr itself. Additional passages for the infusion liquid can be directed transversely of the length of the guide wire for washing the wall of the treated graft. Such transverse passages can be directed primarily transversely but angled proximally for controlling the direction of the flow and ablated particles. Aspiration can be through an outer tube or sheath surrounding the burr-driving flex shaft. The relative amounts of distal infusion, transverse infusion, and aspiration can be controlled to assure that all or essentially all of the infusion liquid and particles carried thereby are ultimately directed proximally to the opening of the aspiration tube.

In another embodiment, the frontal or distal infusion can be through one or more passages in the outer sheath surrounding the flex shaft, or in a distally extending portion of the flex shaft. For infusion through the distal tip of the ablation burr, a valve member can be provided on the guide wire for selectively sealing and opening the distal infusion passage. Different configurations of infusion passages may be used to assure a thorough washing of the treated area.

Distal infusion also can be obtained by a specially designed burr having arcuate or helical grooves which tend to direct the flow of infusion liquid proximally or distally depending on the direction of rotation of the burr. In this construction, the burr can be alternately rotated in one sense and the other sense to first direct infusion liquid distally for washing, then proximally for assuring removal of loose material carried by the infusion liquid.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
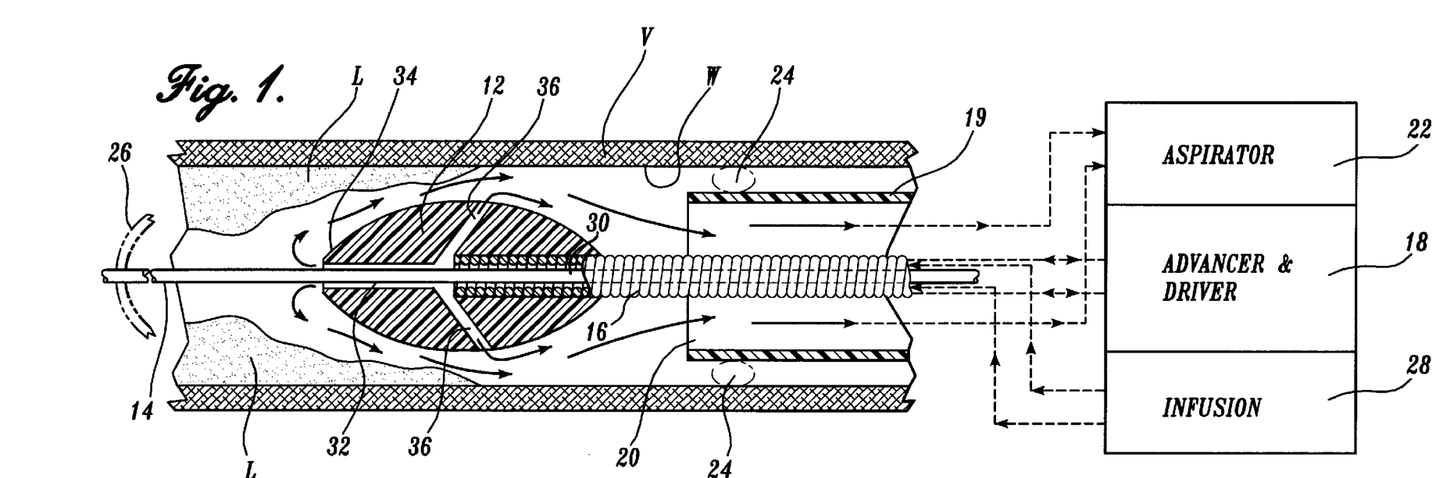
FIG. 1 is a diagrammatic axial section of an occluded blood vessel in the process of treatment by a first embodiment of a system in accordance with the present invention.

With reference to FIG. 1, the system of the present invention is used for treating an occluded blood vessel V, particularly a saphenous vein graft (SVG), having a lesion L. The lesion is ground or broken up by a rotary ablation burr 12 moved along a guide wire 14. The burr is secured to a flex shaft 16 for rotation therewith. For example, the distal end portion of the flex shaft can be secured in an axial socket of the burr. These components are inserted into the vessel and are driven by an external advancer and driver component 18. Component 18 provides the rotational force for the flex shaft 16 and the mechanism for advancing and retracting the flex shaft along the guide wire 14.

The flex shaft 16 can be encircled by an aspiration sheath 19 which can be advanced through the blood vessel by the advancer and driver component 18, preferably independently of movement the drive shaft and burr along the guide wire so as to maintain the distal end or aspiration mouth 20 of the sheath 19 close to the area being treated. An external aspirator 22 includes a vacuum source for drawing fluid and particles into the sheath 19 and externally of the body for disposal. This aspect is quite important when treating vein graft lesions because, unlike native coronary arterial lesions, a predictable release of fine particulate by the action of the abrasive surface of the burr cannot be assumed. Rather, larger and irregular chunks or particles of lesion can break off, and it is important that such larger chunks not be introduced into the body. Thus, it is desirable to isolate the treatment area, such as by an annular balloon 24 or other blocking device to fill the area between the outer periphery of the aspiration sheath 19 and the inner periphery of the vessel V. Similarly, a distal protective or blocking device 26, such as a mechanical balloon, hydraulic balloon or screen, can be deployed in the distal portion of the treatment area.

When aspiration is used, it is desirable to supply or infuse liquid into the treatment area to prevent the vessel V from collapsing. In the present invention, the infusion liquid is supplied from an external infusion component 28. For the embodiment of FIG. 1, the infusion liquid is supplied through the central bore 30 of the flex shaft 16 in the annular space between the flex shaft and the guide wire 14. Thus, the flex shaft forms a conduit for the infusion liquid. As discussed in more detail below, in accordance with the present invention the direction of the infusion liquid in the treatment area is carefully controlled for an additional purpose, namely, washing the treatment area distal to the burr 12 in a controlled manner, in combination with aspiration, so that a maximum amount of ablated material is drawn into the aspiration sheath 19.

Still referring to FIG. 1, burr 12 has an axial passage 32 forming an extension of the bore 30 through the flex shaft 16 and extending distally to the distal end 34 of the burr. In addition, two or more passages 36 extend transversely from the proximal portion of the passage 32 which acts as a plenum for the infusion liquid. Passages 36 can be located in the broader, central portion of the generally oval or elliptical burr 12 and extend at a small acute angle in the proximate direction. The relative sizes of the distal extending passage 32 and transversely extending passages 36 are selected so that the major portion of the infusion liquid is expelled through the transverse passages 36. This can have a washing and scouring effect on the vessel wall W. In addition, a venturi action is created distally of the outer openings of the transverse passages 36, assisted by the degree of aspiration induced at the mouth 20 of the aspiration tube 19. Consequently, the smaller amount of infusion liquid exiting at the distal end 34 of the burr is also drawn rearward along the burr and into the aspiration sheath. Nevertheless, the distally directed infusion liquid washes the treated area for carrying loose particles to the mouth of the aspiration sheath.

The burr 12 can be advanced and retracted along the guide wire for gradually grinding and breaking up the lesion L. In addition, the back and forth movement of the burr along the guide wire can be used for washing the treated area and inner wall W of the vein V to increase the particle-removing efficiency of the system in accordance with the present invention. Ultimately, the burr will reach the distal blocking device 26. At this point the distally directed infusion liquid cooperates with the blocking device to achieve a complete washing of the treatment area. Alternatively, it is envisioned that the degree of distal or frontal infusion and transverse infusion can be controlled so as to eliminate the need for a proximate blocking device 26, while still ensuring that particles ground, broken, or loosened by the action of the rotating burr are swept up by the infusion liquid and carried rearward into the aspiration tube. In a representative embodiment, the amount of distal or frontal infusion can be about 5% to about 45% of the total amount of infusion liquid, but the amount used for a particular application also depends on the strength of aspiration and whether or not a distal blocking device is used.

In the embodiment of FIG. 1, the burr fits somewhat loosely on the guide wire 14 due to the larger diameter of the distal passage 32. In a representative embodiment, the clearance between the guide wire and the inner periphery of the passage 32 can be up to about 0.012 inch radially. Known burrs have a maximum clearance of about 0.006 inch radially for a close fit of the burr on the guide wire. Thus, the gap for this embodiment of the present invention is at least doubled. In addition to the advantageous effects described above, the infusion liquid can provide a lubricating effect of the burr on the guide wire, reducing friction that could cause overheating or increase the likelihood of weakening of the guide wire.

Figure 2:
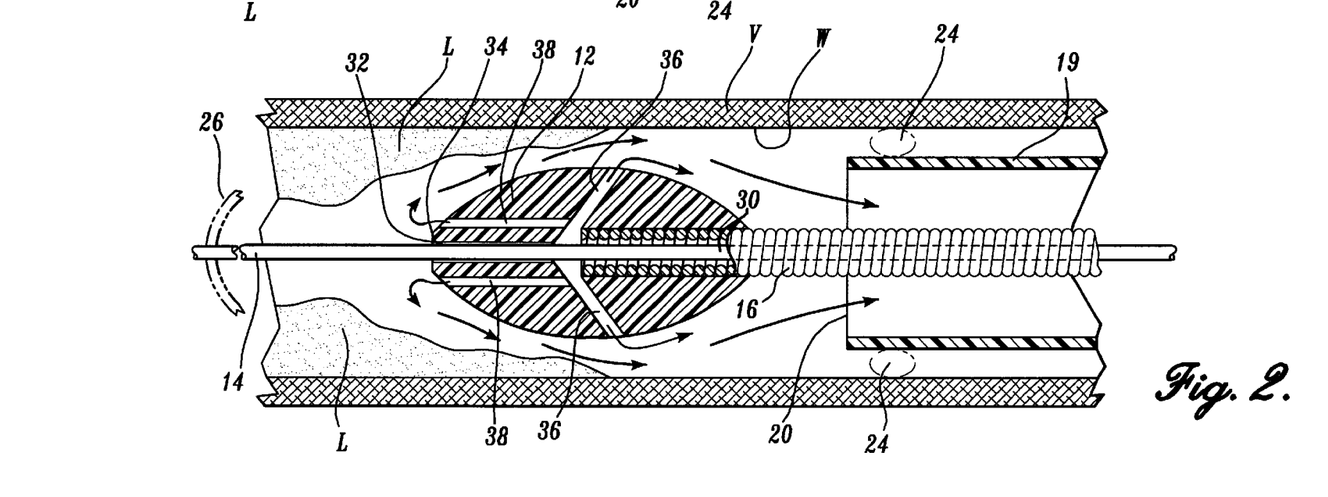
FIG. 2 is a section corresponding to FIG. 1 showing treatment of the vessel by a second embodiment of the present invention.

In the embodiment of FIG. 2, the burr 12 fits more closely on the guide wire 14, i.e., the passage 32 has a tighter clearance, similar to known burrs. Distal infusion can be achieved by one or more axially extending passages 38, spaced radially outward from the central passage 32. Nevertheless, preferably the passages 38 open close to the distal end 34 of the burr so that a minor portion of the infusion liquid, such as about 5% to about 45% of the total, is directed distally to achieve the desirable effects described above. In other respects, the embodiment of FIG. 2 is identical to the embodiment of FIG. 1, including external components for advancing and driving the burr and the aspiration sheath 19, aspiration component, infusion component, and proximate and distal blocking devices 24 and 26.

Figure 3:
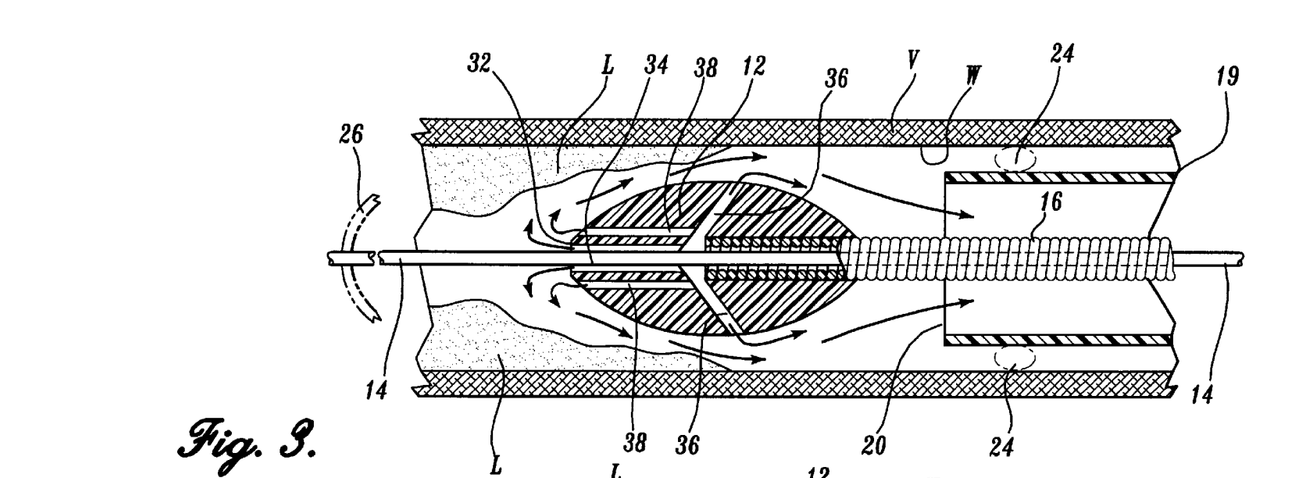
FIG. 3 is a section corresponding to FIG. 1 showing treatment by a third embodiment of the present invention.

As illustrated in FIG. 3, passages 38 also can be used in combination with a larger passage 32 of the type described with reference to FIG. 1, so that frontal infusion is achieved both along the central axis of the burr 12 and at one or more locations spaced radially outward. In all instances, the major portion of infusion liquid is expelled from the openings of the transverse passages 36, so that the jetting action of infusion liquid expelled through passages 36 washes and potentially scours the vessel wall W in addition to directing particles carried by the infusion liquid to the mouth 20 of the aspiration sheath 19. In other respects the embodiment of FIG. 3 is identical to the embodiment of FIG. 1, including the external components for driving the flex shaft 16, advancing the flex shaft and aspiration sheath 19, supplying infusion liquid, and aspirating liquid and particles from the treatment area, in addition to the proximate and, optionally, distal blocking devices 24 and 26.

Figure 4:
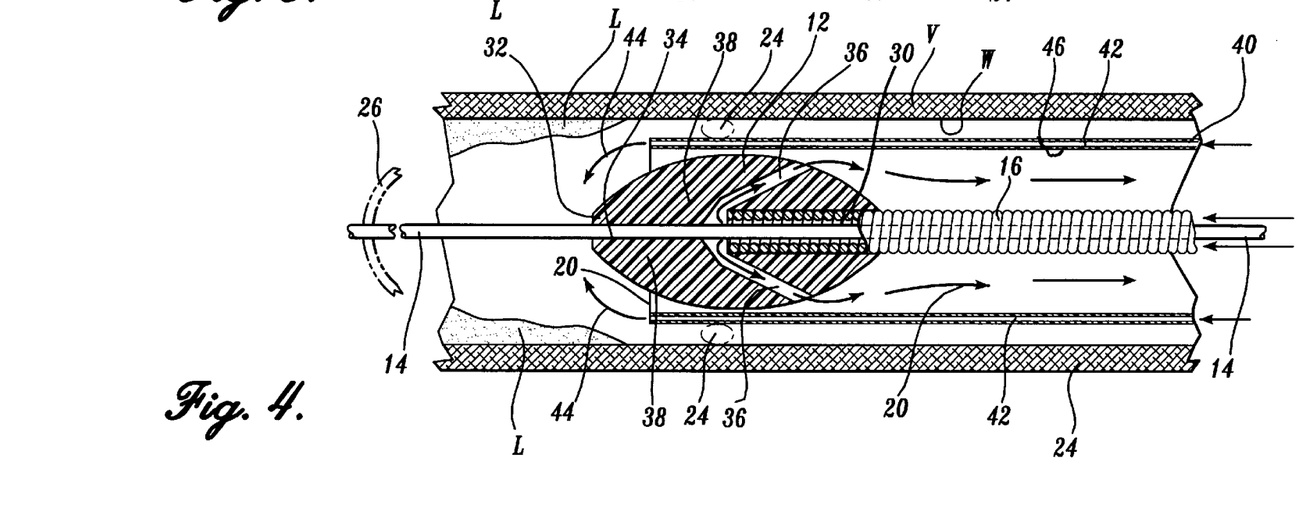
FIG. 4 is a section corresponding to FIG. 1 showing treatment by a fourth embodiment of the present invention.

In the embodiment of FIG. 4, the burr 12 driven by flex shaft 16 fits more tightly on the guide wire 14 so that no appreciable amount of infusion liquid is supplied through the distal end portion 34 of the burr. Rather, a modified aspiration sheath 40 is provided with passages or conduits 42 for infusion liquid supplied by the external infusion component. Such passages exit at the distal end 20 of the sheath as indicated by the arrows 44. Aspiration is through the center part of the sheath, i.e., that part radially inward of the inner periphery 46. In addition to being supplied through the passages 42, infusion liquid still is supplied through the central bore 30 of the flex shaft 16. This portion of the infusion liquid, which constitutes the major portion, such as about 55% to about 95% of the total, is directed through transversely extending passages 36 of the burr, which can be angled rearward or proximally. In this embodiment, the burr can be rotated and advanced along the guide wire 14 for treating the lesion L. During the procedure, the sheath 40 can be advanced to expel infusion liquid distally for washing the treated area. The burr can be retracted into the sheath 40 at this time, and then projected distally so as not to interfere with aspiration of the fluid and ablated particles carried thereby. With sheath 40 retracted, infusion liquid from the passages 36 washes and scours the vessel wall W and assists in directing the infusion liquid and particles into the aspirating central portion of the sheath. Preferably the system in accordance with FIG. 4 is used with proximal and distal blocking devices 24 and 26. As in the previously described embodiments, the fit of the sheath 40 in the proximate blocking device 24 should be a sliding fit so that the sheath can be advanced and retracted relative to the blocking device, without allowing infusion liquid or particles to pass between the blocking device and the exterior of the sheath. Sheath 40 can be formed with discrete passages 42. Alternatively, a continuous passage can be formed between inner and outer walls of the sheath. In other respects, the embodiment of FIG. 4 is identical to the embodiment of FIG. 1.

Figure 5:
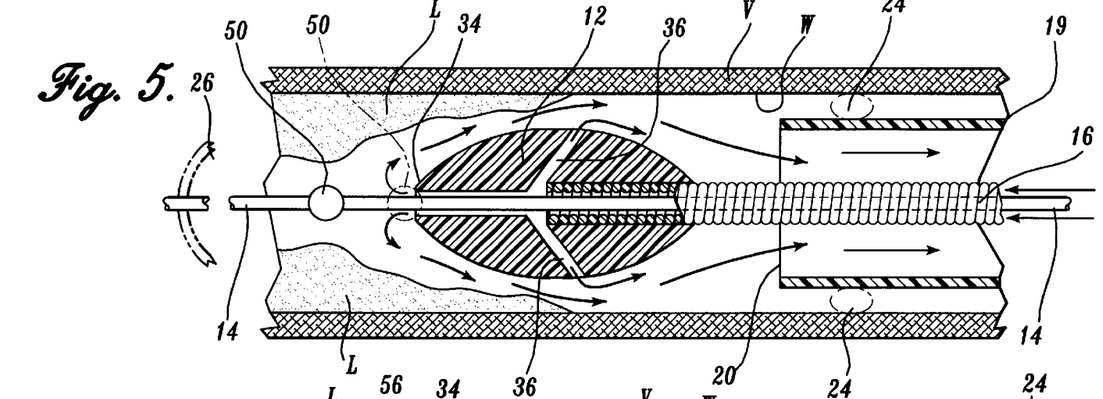
FIG. 5 is a section corresponding to FIG. 1 showing treatment by a fifth embodiment of the present invention.

FIG. 5 illustrates an embodiment identical to the embodiment of FIG. 1 except for the inclusion of an enlarged valve member 50 on the guide wire 14 at a location distally of the burr 12. The guide wire can be moved fore and aft in the vein V for selectively engaging the distal end 34 of the burr and thereby blocking the distally extending infusion passage 34. In this way, the frontal or distal infusion can be controlled. For example, with the valve member 50 closing the distal end of the burr, the burr and guide wire can be manipulated together for abrading the lesion L. When a desired degree of ablation has occurred, the guide wire can be moved distally to open the distal end of the infusion passage 32 and wash the treating area. Regardless of whether or not distal infusion is occurring, infusion liquid exits through the transverse passages 36, both for washing the vessel wall W and for maintaining sufficient liquid in the treatment area to prevent collapse of the vessel while aspiration is occurring through the sheath 19.

Figure 6:
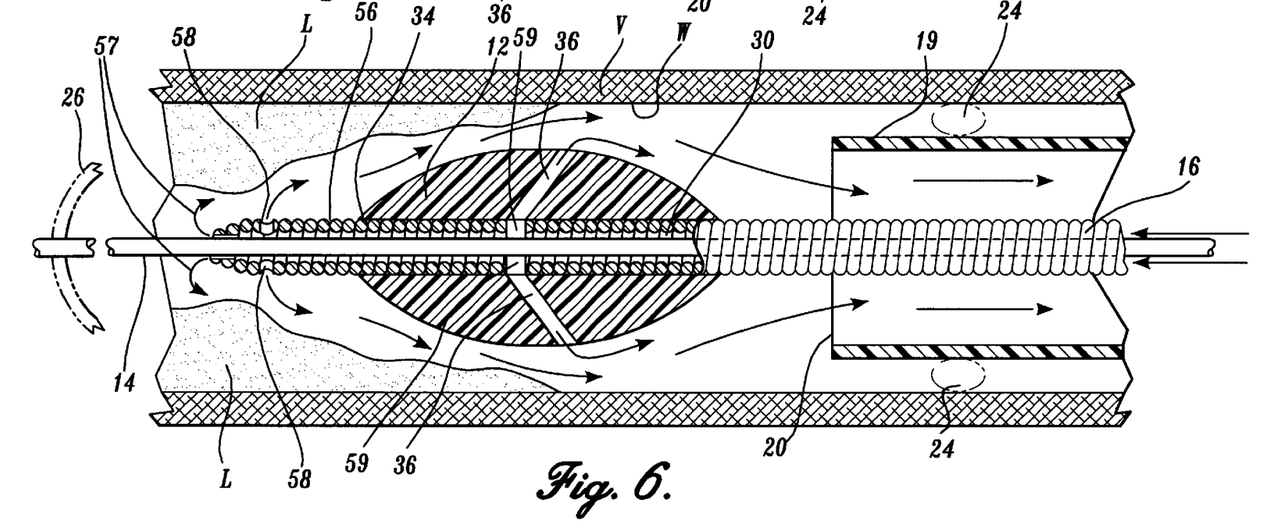
FIG. 6 is a section corresponding to FIG. 1 showing treatment by a sixth embodiment of the present invention.

Another way to achieve washing infusion distally of the burr 12 is illustrated in FIG. 6. In that embodiment, the burr 12 is secured on the flex shaft 16, but the shaft extends a substantial distance forward of the distal end 34 of the burr. The flex shaft fits loosely on the guide wire 14 so that infusion liquid passes through the central bore 30 of the flex shaft and through its projecting distal end portion 56, as indicated by arrows 57. Transverse passages 58 can be provided at a location proximate to the distal end of the shaft but still forward of the burr 12. As in all previous embodiments, the major portion of the infusion liquid is expelled transversely through passages 36, and the degree of aspiration is controlled to assure that even the distally expelled infusion liquid is drawn back into the mouth 20 of the aspiration tube 19. The flex shaft also has passages 59 aligned with transverse passages 36 in the burr. For a construction as shown in FIG. 6, any distal blocking device 26 should be deployed sufficiently forward of the lesion L that the burr is effective to act on the entire lesion, despite the distally projecting portion of the flex shaft.

Figures 7, 8A, 8B:
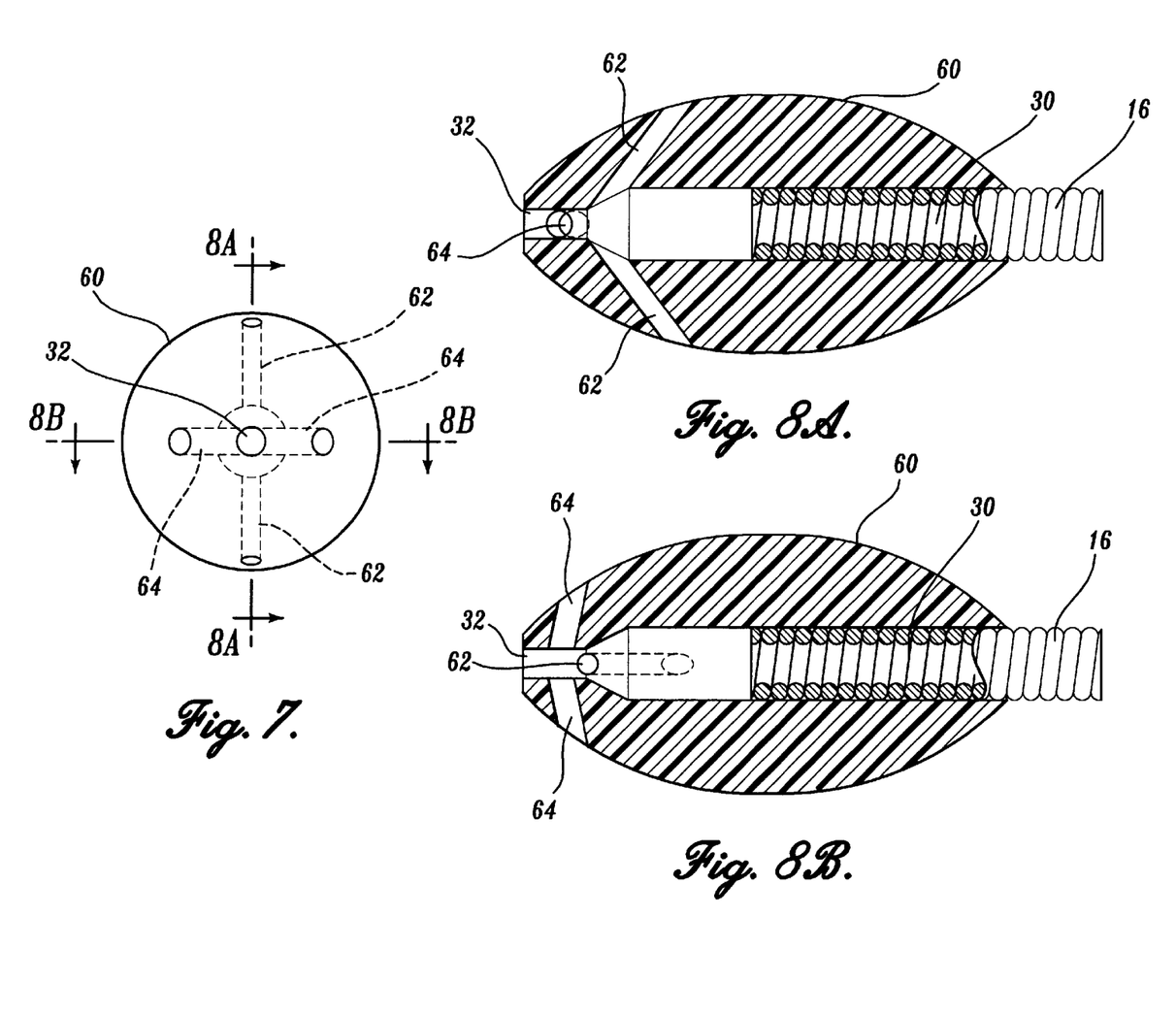
FIG. 7 is a distal end elevation of a modified burr usable in the system of the present invention.
FIG. 8A is a side elevation thereof with parts shown in section along line 8A—8A of FIG. 7.
FIG. 8B is a top plan thereof with parts shown in section along line 8B—8B of FIG. 7.

The modified burr 60 shown in FIGS. 7, 8A, and 8B, is secured to and driven by a flex shaft 16, similar to the system of FIG. 1. For example, the flex shaft and burr would be advanced and retracted along a guide wire, by means of an external advancer and driver component. Infusion is through the central bore 30 of the flex shaft by an external infusion component. Aspiration is through an aspiration sheath fitted around the flex shaft. Proximate and distal blocking devices can be provided for the area to be treated.

Burr 60 has two sets of transverse passages 62 and 64. Diametrically opposed passages 64 toward the distal end 70 of the burr extend almost radially, but are angled slightly proximally. Passages 62 extend transversely at a larger angle in the proximate direction, and to the rear of the passages 64. In use, infusion liquid through the passages 64 is more effective in removing lesion particles and scouring the vessel wall due to the more direct jetting action. The jet action from the passages 62 is most effective in pushing the liquid mixed with debris proximally so that the aspirating sheath can easily pick up the debris. A small degree of frontal infusion can be provided by sizing the axial bore 32 of the burr to fit more or less loosely on the guide wire. Alternatively, additional distally directed passages can be provided spaced radially outward from the axial bore.

Figure 9A:
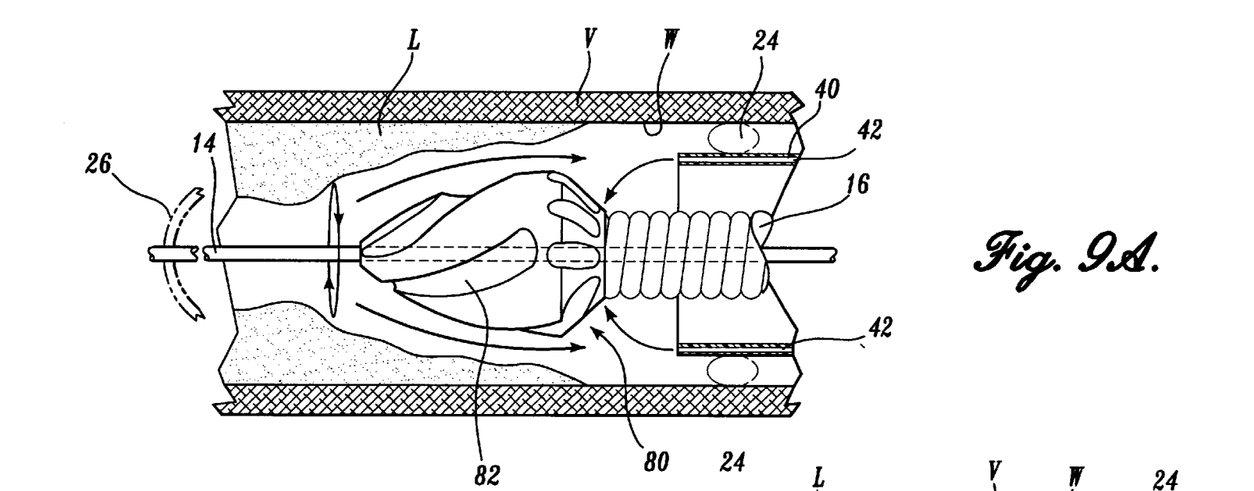
FIG. 9A and FIG. 9B are sections corresponding to FIG. 1 showing treatment by an additional embodiment of the present invention.
Figure 9B:
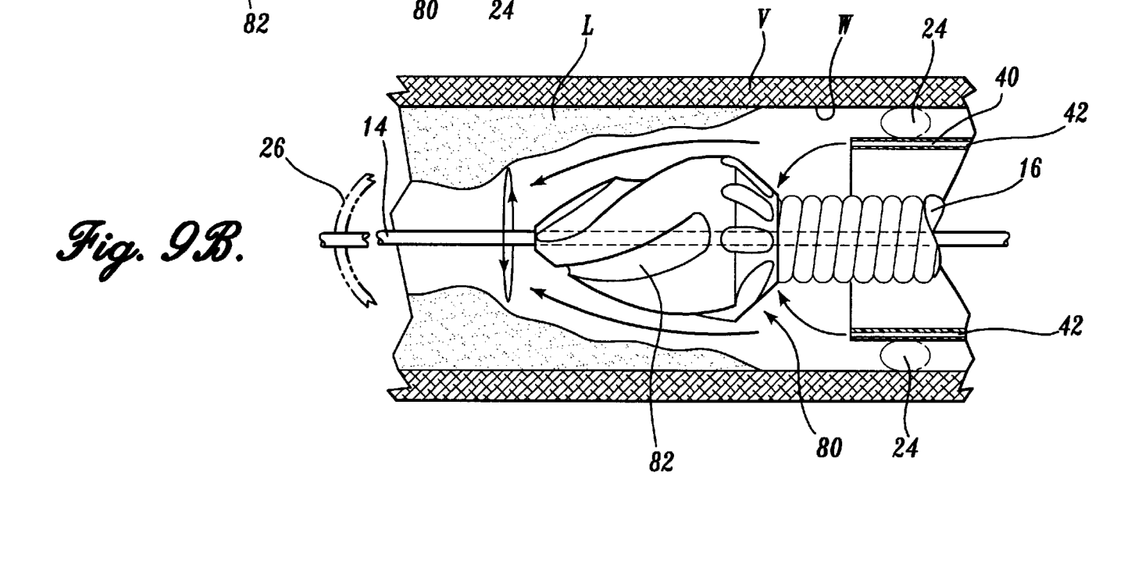

Another modified burr 80 is illustrated in FIGS. 9A and 9B. Such a burr is driven by a flex shaft 16 on which the burr is secured, the burr and flex shaft being movable along a guide wire 14. An aspiration sheath 40 is provided proximate to the burr, with a proximate blocking device 24.

Burr 80 is provided with a series of arcuate, partially helical grooves 82. The grooves are sufficiently deep that they affect the flow of infusion liquid contained within the vessel V. For example, when the burr is rotated in one sense as indicated in FIG. 9B, infusion liquid is driven in propeller fashion in a distal direction, whereas when the burr is driven in the opposite sense as illustrated in FIG. 9A the infusion liquid is driven in propeller fashion in the opposite direction. The infusion liquid can be supplied to the treatment site through a passage or passages 42 in the sheath 40, with aspiration selectively applied through the central portion of the sheath. The direction of rotation of the burr can be reversed frequently at the same time that the burr acts on the lesion, to alternately wash the treated area and assist in conveying debris-carrying infusion liquid proximally to the opening of the aspiration sheath.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A frontal infusion system for treating a blood vessel lesion comprising:
   a burr having a distal end and a proximate end, the burr being moveable through a blood vessel containing a lesion for ablating the lesion;
   a conduit connected to the burr to carry a quantity of infusion liquid thereto, the burr having one or more first passages extending at least partly in a proximate direction for expelling infusion liquid at least partly toward the proximate end portion of the burr;

one or more second passages for conveying infusion liquid and constructed and arranged relatively to expel such infusion liquid beyond the distal end of the burr, the first passages and the second passages being constructed and arranged relatively such that more infusion fluid is expelled through the first passages than through the second passages; and an aspiration sheath having an aspiration mouth opening adjacent to the burr for aspiration of inflsion liquid expelled from the first passages and from the second passages.

2. The system of claim 1, in which the burr is sized for retraction into the aspiration sheath.

3. The system of claim 1, in which the aspiration sheath has a circumferential wall, the one or more second passages extending through and along the circumferential wall of the aspiration sheath.

4. The system of claim 1, including a flex shaft connected to the burr for driving the burr, the flex shaft having a central bore forming the conduit for carrying infusion liquid to the burr.

5. The system of claim 4, in which the shaft has a portion extending distally beyond the distal end of the burr, said portion having the one or more second passages.

6. The system of claim 5, in which the first passages of the burr and the second passages are constructed and arranged relatively so that about 5% to about 45% of the infusion liquid is expelled distally of the burr.

7. The system of claim 1, in which the first passages of the burr and the second passages are constructed and arranged relatively so that about 5% to about 45% of the infusion liquid is expelled distally of the burr.

8. A frontal infusion system for use in treating a blood vessel lesion comprising:

a burr having a distal end and a proximate end, the burr being movable through a blood vessel containing a lesion for ablating the lesion;

a conduit connected to the burr to carry a quantity of infusion liquid thereto, the burr having a plurality of passages for expelling infusion liquid received from the conduit, said passages including at least one first passage extending at an angle in the proximate direction for expelling infusion liquid at least partly in a proximate direction and one or more second passages extending distally for expelling infision liquid from the distal end portion of the burr, the first and second passages being constructed and arranged relatively such that the major portion of the infusion liquid is expelled through the at least one first passage and a minor portion is expelled through the one or more second passages; and an aspiration sheath having an aspiration mouth opening adjacent to the burr for aspiration of infusion liquid expelled from the first and second passages of the burr.

9. The system of claim 8, in which the burr has an axial bore for receiving a guide wire and for guiding movement of the burr along the guide wire.

10. The system of claim 9, in which the axial bore forms the second passage for expelling infusion liquid from the distal end portion of the burr.

11. The system of claim 8, in which the second passage for expelling infusion liquid is separate from the axial bore of the burr and is spaced radially outward therefrom.

12. The system of claim 8, in which the first and second passages are constructed and arranged relatively so that about 5% to about 45% of the infusion liquid from the conduit is expelled distally of the burr.

13. The system of claim 12, including a flex shaft connected to the burr for driving the burr, the flex shaft having a central bore forming the conduit for carrying the infusion liquid.

14. The system of claim 8, including a valve for opening and closing the first passage.

15. The system of claim 14, including a guide wire extending through the blood vessel, the burr having an axial bore for receiving the guide wire for movement therealong, the valve including an enlargement on the guide wire that can be selectively positioned to open and close a distal end portion of the first passage.

* * * * *

UNITED STATES PATENT AND TRADEMARK OFFICE
CERTIFICATE OF CORRECTION

PATENT NO. : 6,491,660 B2
DATED : December 10, 2002
INVENTOR(S) : Z. Guo et al.

It is certified that error appears in the above-identified patent and that said Letters Patent is hereby corrected as shown below:

Title page,
Item [56], References Cited, U.S. PATENT DOCUMENTS, insert in appropriate order:
-- 6,154,724    10/1992        Andrews --
Item [57], ABSTRACT,
Line 6, "burr, In" should read -- burr. In --

Column 7,
Line 9, "inflsion" should read -- infusion --

Column 8,
Line 5, "infision" should read -- infusion --

Signed and Sealed this

Fifteenth Day of April, 2003

JAMES E. ROGAN
*Director of the United States Patent and Trademark Office*